United States Patent
Denison et al.

(10) Patent No.: US 10,052,486 B2
(45) Date of Patent: Aug. 21, 2018

(54) TIMED DELIVERY OF ELECTRICAL STIMULATION THERAPY

(71) Applicant: Medtronic, Inc., Minneapolis, MN (US)

(72) Inventors: Timothy J. Denison, Minneapolis, MN (US); Scott R. Stanslaski, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 136 days.

(21) Appl. No.: 15/071,835

(22) Filed: Mar. 16, 2016

(65) Prior Publication Data

US 2016/0287879 A1    Oct. 6, 2016

Related U.S. Application Data

(60) Provisional application No. 62/143,590, filed on Apr. 6, 2015.

(51) Int. Cl.
*A61N 1/00* (2006.01)
*A61N 1/36* (2006.01)
(Continued)

(52) U.S. Cl.
CPC ........ *A61N 1/36167* (2013.01); *A61B 5/4082* (2013.01); *A61B 5/4836* (2013.01); *A61N 1/36025* (2013.01); *A61N 1/36067* (2013.01); *A61N 1/36139* (2013.01); *A61N 1/36171* (2013.01); *A61B 5/048* (2013.01); *A61B 5/1101* (2013.01); *A61B 5/7225* (2013.01); *A61B 2562/0219* (2013.01); *A61N 1/0534* (2013.01); *A61N 1/36053* (2013.01);
(Continued)

(58) Field of Classification Search
USPC ....................................... 607/3, 62
See application file for complete search history.

(56) References Cited

U.S. PATENT DOCUMENTS

| 6,066,163 A | 5/2000 | John |
| 6,456,887 B1 | 9/2002 | Dudding et al. |

(Continued)

FOREIGN PATENT DOCUMENTS

| WO | 2012163347 A1 | 12/2012 |
| WO | 2013158208 A2 | 10/2013 |

(Continued)

OTHER PUBLICATIONS

Brittain et al., "Tremor Suppression by Rhythmic Transcranial Current Stimulation," Current Biology, vol. 23, Elsevier Ltd, Mar. 4, 2013, pp. 436-440.

(Continued)

*Primary Examiner* — Nicole F Johnson
*Assistant Examiner* — Nicole F. Lavert
(74) *Attorney, Agent, or Firm* — Shumaker & Sieffert, P.A.

(57) ABSTRACT

In some examples, a phase locked loop (PLL) circuit outputs a timing signal having a frequency and phase that is the same as a patient signal that is an input to the PLL circuit. The PLL circuit includes or is coupled to a storage circuit that stores information needed to cause the PLL circuit to maintain the frequency of the timing signal to the same frequency even after the patient signal is not available as an input.

20 Claims, 7 Drawing Sheets

(51) Int. Cl.
*A61B 5/00* (2006.01)
*A61B 5/048* (2006.01)
*A61B 5/11* (2006.01)
*A61N 1/05* (2006.01)

(52) U.S. Cl.
CPC ...... *A61N 1/36064* (2013.01); *A61N 1/36082* (2013.01); *A61N 1/36096* (2013.01)

(56) References Cited

U.S. PATENT DOCUMENTS

| | | | |
|---|---|---|---|
| 6,771,133 | B2 | 8/2004 | Lautzenhiser |
| 7,110,820 | B2 | 9/2006 | Tcheng et al. |
| 7,239,918 | B2 | 7/2007 | Strother et al. |
| 2009/0018609 | A1 | 1/2009 | DiLorenzo |
| 2011/0184489 | A1 | 7/2011 | Nicolelis et al. |
| 2011/0201977 | A1* | 8/2011 | Tass ............... A61H 7/004 601/15 |
| 2012/0101547 | A1 | 4/2012 | Jensen et al. |
| 2012/0277820 | A1 | 11/2012 | Wu et al. |
| 2014/0296752 | A1 | 10/2014 | Edgerton et al. |
| 2014/0316484 | A1 | 10/2014 | Edgerton et al. |
| 2014/0336722 | A1 | 11/2014 | Rocon De Lima et al. |
| 2016/0147964 | A1 | 5/2016 | Corey et al. |

FOREIGN PATENT DOCUMENTS

| | | |
|---|---|---|
| WO | 2014113813 A1 | 7/2014 |
| WO | 2014198943 A1 | 12/2014 |

OTHER PUBLICATIONS

Cagnan et al., "Phase dependent modulation of tremor amplitude in essential tremor through thalamic stimulation," Brain, A Journal of Neurology, Sep. 14, 2013, 14 pp.

Modolo et al., "Past, present and future of brain stimulation," Mathematical Modelling of Natural Phenomena, vol. 5, No. 2, 2009, 21 pp. (Applicant points out, in accodance with MPEP 609.04(a), that the year of publication, 2009, is sufficiently earlier than the effective U.S. filing date, Apr. 6, 2015, so that the particular month of publication is not in issue.).

Santaniello et al., "Closed-Loop Control of Deep Brain Stimulation: A Simulation Study," IEEE Transactions on Neural Systems and Rehabilitation Engineering, vol. 19, No. 1, Feb. 2011, pp. 15-24.

International Search Report and Written Opinion of International Application No. PCT/US2016/024128, dated Jul. 1, 2016, 13 pp.

* cited by examiner

TIMED DELIVERY OF ELECTRICAL STIMULATION THERAPY

This application claims the benefit of U.S. Provisional Patent Application No. 62/143,590, filed Apr. 6, 2015, the entire content of which is hereby incorporated herein by reference.

TECHNICAL FIELD

The disclosure relates to therapy delivery by a medical device.

BACKGROUND

Medical devices, such as electrical stimulators or therapeutic agent delivery devices, may be used in different therapeutic applications, such as deep brain stimulation (DBS), spinal cord stimulation (SCS), pelvic stimulation, gastric stimulation, peripheral nerve stimulation, functional electrical stimulation or delivery of pharmaceutical agent, insulin, pain relieving agent or anti-inflammatory agent to a target tissue site within a patient. A medical device may be configured to deliver therapy to a patient to treat a variety of symptoms or patient conditions such as chronic pain, tremor, Parkinson's disease, other types of movement disorders, seizure disorders (e.g., epilepsy), urinary or fecal incontinence, sexual dysfunction, obesity, mood disorders, gastroparesis or diabetes.

In some therapy systems, an electrical stimulator, which may be implantable in some instances, delivers electrical therapy to a target tissue site within a patient with the aid of one or more electrodes, which may be deployed by medical leads, on a housing of the electrical stimulator, or both. In addition to or instead of electrical stimulation therapy, a medical device, which may be implantable in some instances, may deliver a therapeutic agent to a target tissue site within a patient with the aid of one or more fluid delivery elements, such as a catheter or a therapeutic agent eluting patch.

SUMMARY

The disclosure describes example systems, devices, and methods for maintaining the correct timing of electrical stimulation therapy delivery (e.g., phase and frequency of when to deliver therapy) even when symptom relief is achieved for the condition for which the therapy is delivered. For example, in a closed-loop system, a sensed signal forms the input from which a medical device determines the timing of when to deliver therapy. However, the delivery of the therapy may squelch the sensed signal that forms the input, resulting in loss of the signal used to determine the timing of therapy delivery.

In examples described in this disclosure, a phase locked loop (PLL) circuit may track the phase of the input signal, and output a timing signal that is locked to the input signal (e.g., the frequency of the timing signal is approximately equal to or a set multiple of the input signal). In addition, the PLL circuit may include or be coupled to a storage unit configured to store information to cause the PLL circuit to maintain the frequency of the timing signal at approximately the same frequency even after the input signal is no longer available (e.g., not present, not being received, etc.). The medical devices controls delivery of therapy based on the timing signal. In this manner, the medical device may be able to provide therapy at the correct instances even if the signal used to determine the timing of therapy delivery is not available.

In one example, the disclosure describes a method comprising receiving a patient signal indicative of a patient condition, determining a timing signal having a frequency based on the patient signal, during a duration when the patient signal is not being received, outputting the timing signal having the same frequency as the frequency of the timing signal determined based on the patient signal, and controlling delivery of electrical stimulation therapy based on the outputted timing signal during at least a portion of the duration when the patient signal is not being received.

In one example, the disclosure describes a medical device comprising a circuit configured to receive a patient signal indicative of a patient condition, determine a timing signal having a frequency based on the patient signal, and during a duration when the patient signal is not being received, output the timing signal having the same frequency as the frequency of the timing signal determined based on the patient signal, and an electrical stimulation generator configured to deliver therapy based on the timing signal during at least a portion of the duration when the patient signal is not being received.

In one example, the disclosure describes a medical device comprising means for receiving a patient signal indicative of a patient condition, means for determining a timing signal having a frequency based on the patient signal, means for outputting the timing signal having the same frequency as the frequency of the timing signal determined based on the patient signal during a duration when the patient signal is not being received, and means for controlling delivery of therapy based on the outputted timing signal during at least a portion of the duration when the patient signal is not being received.

The details of one or more examples are set forth in the accompanying drawings and the description below. Other features, objects, and advantages will be apparent from the description and drawings, and from the claims.

DETAILED DESCRIPTION

Figure 1:
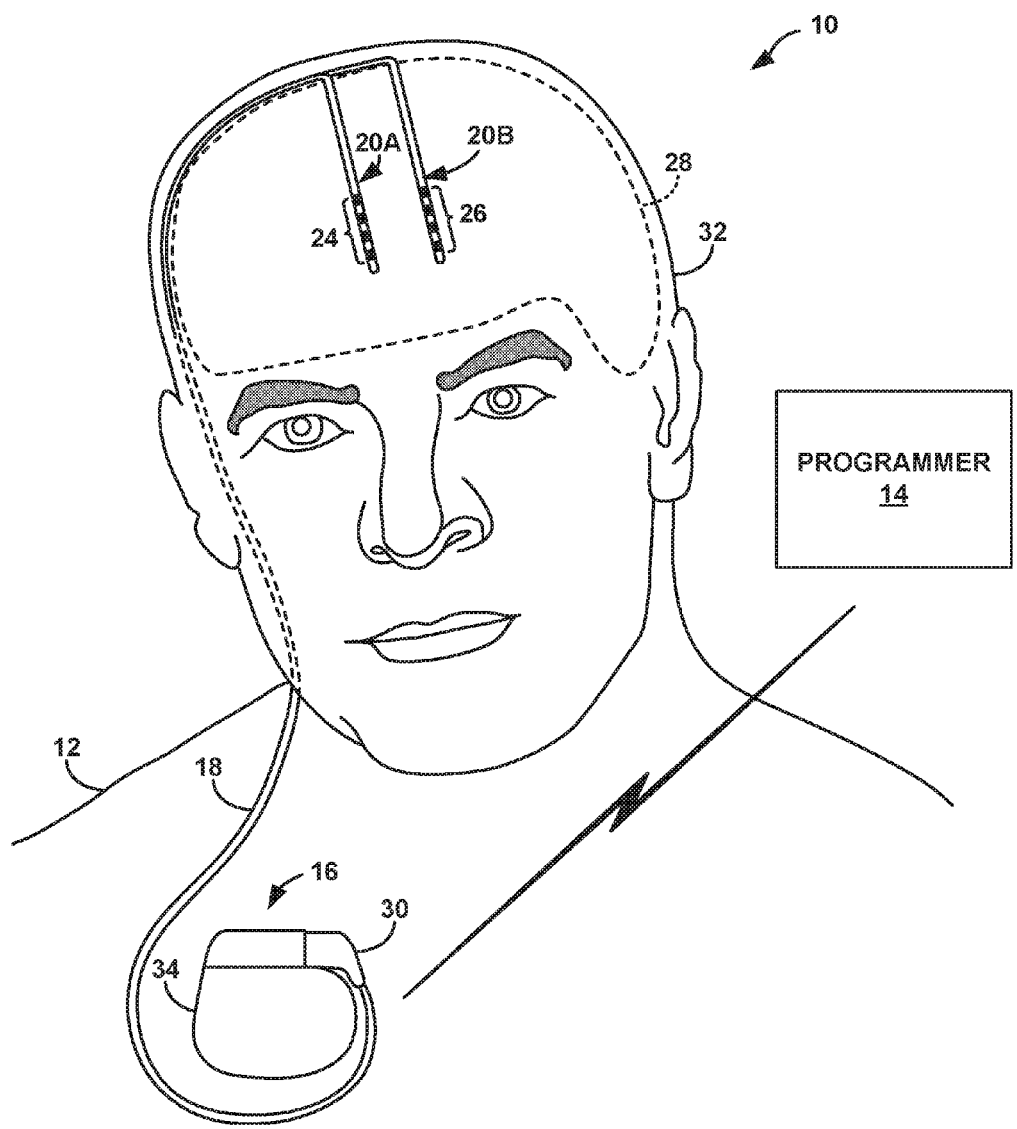
FIG. 1 is a conceptual diagram illustrating an example deep brain stimulation (DBS) system configured to sense a bioelectrical brain signal and deliver electrical stimulation therapy to a tissue site within a brain of a patient.

The disclosure describes example systems, devices, and methods for maintaining a frequency of a timing signal used to determine when therapy is delivered. The timing signal may be generated from a sensed patient signal. Examples of the patient signal include an output signal from an accelerometer, a bioelectrical brain signal, or other types of physiological signals either produced by the patient due to a patient condition or generated from a patient condition (e.g., an electrical signal representing patient tremor).

A medical device, such as an implantable medical device (IMD), utilizes the timing signal to determine when to deliver therapy. As an example, the medical device may deliver therapy at a peak and/or trough of the timing signal. Accordingly, the frequency and phase of the timing signal may determine when the medical device delivers therapy. In this manner, the medical device may deliver therapy in a closed-loop fashion, where the therapy delivery is based on the patient signal.

The medical device may utilize a phase locked loop (PLL) circuit to generate the timing signal based on the patient signal. The PLL circuit includes a reference oscillator that outputs the timing signal. The patient signal may be an input into the PLL circuit, and the difference between the patient signal and the timing signal controls the frequency the timing signal that the reference oscillator outputs. The PLL circuit may adjust the frequency of the timing signal until the difference between the patient signal and the timing signal is small (e.g., approximately zero). In this manner, the frequency and the phase of the timing signal are approximately equal to the frequency and phase of the patient signal.

In accordance with the techniques described in this disclosure, the PLL circuit may include or may be coupled to a storage circuit that stores information used to maintain the frequency and phase of the timing signal in the event that the patient signal is no longer available. For instance, the frequency of the signal that the reference oscillator outputs may be based on the voltage level received by the reference oscillator, and in the case for a particular voltage level (e.g., X volts), the frequency of the timing signal is the same as the frequency of the patient signal. As one example, the storage circuit may be an integrator that outputs the same voltage as the voltage needed to keep the frequency of the timing signal at the same or substantially the same level as the frequency of the patient signal even if the patient signal is no longer available. In other words, the integrator, which is one example of a storage circuit, outputs a voltage level of X volts, which causes the PLL circuit to output at a particular frequency, even when the patient signal is no longer available so that frequency of the timing signal is the same as the frequency of the patient signal, when the patient signal was available (e.g., not being currently sensed such as during delivery of stimulation).

The medical device may then determine when to deliver therapy (e.g., a burst of pulses at a particular burst frequency) based on the timing signal, and potentially deliver regular timed therapy. In this manner, even if the patient signal is no longer available, the medical device can still deliver therapy at the correct times (e.g., at peaks and/or troughs of the timing signal).

For example, in some cases, it may be possible for the patient signal to be used directly as the timing signal. In such examples, the medical device may determine when to deliver therapy based on the patient signal (e.g., determine when a peak and/or trough exists in the sensed patient signal, and deliver a therapy during a peak and/or trough or at a predetermined time delay relative to the peak and/or trough). The delivery of therapy may provide symptom relief, but a result of symptom relief may be loss of the patient signal. Because the medical device relied on the patient signal to determine when to deliver therapy, the loss of the patient signal may result in the medical device delivering therapy at suboptimal times.

As an example, an accelerometer may output a patient signal whose frequency is based on tremors of a patient with Parkinson's disease. In one case, the medical device would use the patient signal to determine when to deliver therapy, and deliver therapy accordingly. The result of the therapy delivery is a reduction in the tremors. However, it was the tremors that determined when therapy should be delivered. If the tremors are not present, then there may be no patient signal, and if there is no patient signal, the medical device may deliver therapy at suboptimal times, which may potentially cause the tremors to return.

By utilizing a PLL circuit and a storage circuit, the medical device may be able to store information needed to ensure that the frequency of the timing signal is kept relatively constant even after the patient signal is no longer available due to proper therapy delivery (e.g., electrical stimulation therapy). Accordingly, the medical device may be able to deliver therapy at the correct times to reduce the chances of symptoms returning after initially achieving symptom relief.

In some cases, even with the storage circuit, the timing of the therapy delivery may become suboptimal. As one example, characteristics of the tremors may change. In this case, the patient signal may no longer be zero, and the PLL circuit may receive a patient signal. The PLL circuit may then adjust the voltage level of the reference oscillator to output an updated timing signal that better tracks the patient signal, and the timing of the electrical stimulation therapy delivery can be based on the updated timing signal. In other words, any perturbations, after initial squelching of the patient signal, will continuously nudge frequency of the timing signal so that the medical device delivers therapy at the correct times.

FIG. 1 is a conceptual diagram illustrating an example therapy system 10 that is configured to deliver therapy to patient 12 to manage a disorder of patient 12. In some examples, therapy system 10 may deliver therapy to patient 12 to manage a movement disorder or a neurodegenerative impairment of patient 12. Patient 12 ordinarily will be a human patient. In some cases, however, therapy system 10 may be applied to other mammalian or non-mammalian non-human patients. A movement disorder may be characterized by one or more symptoms, such as, but not limited to, impaired muscle control, motion impairment or other movement problems, such as rigidity, bradykinesia, rhythmic hyperkinesia, non-rhythmic hyperkinesia, dystonia, tremor, and akinesia. In some cases, the movement disorder may be a symptom of Parkinson's disease or Huntington's disease. However, the movement disorder may be attributable to other patient conditions.

Although movement disorders are primarily referred to throughout the remainder of the application, in other examples, therapy system 10 may be configured to deliver therapy to manage other patient conditions, such as, but not limited to, seizure disorders (e.g., epilepsy), psychiatric disorders, behavior disorders, mood disorders, memory disorders, mentation disorders, Alzheimer's disease, or other neurological or psychiatric impairments, in addition to or instead of a movement disorder. Examples of psychiatric disorders include major depressive disorder (MDD), bipolar disorder, anxiety disorders, post traumatic stress disorder, dysthymic disorder, and obsessive compulsive disorder (OCD). Treatment of other patient disorders via delivery of therapy to brain 28 or another suitable target therapy delivery site in patient 12 are also contemplated.

In the example shown in FIG. 1, therapy system 10 includes medical device programmer 14, implantable medical device (IMD) 16, lead extension 18, and one or more leads 20A and 20B (collectively "leads 20") with respective sets of electrodes 24, 26. IMD 16 includes a therapy module that includes a stimulation generator that is configured to generate and deliver electrical stimulation therapy to one or more regions of brain 28 of patient 12 via a subset of electrodes 24, 26 of leads 20A and 20B, respectively. In the example shown in FIG. 1, therapy system 10 may be referred to as a deep brain stimulation (DBS) system because IMD 16 provides electrical stimulation therapy directly to tissue within brain 28, e.g., a tissue site under the dura mater of brain 28 or one or more branches or nodes, or a confluence of fiber tracks. In other examples, leads 20 may be positioned to deliver therapy to a surface of brain 28 (e.g., the cortical surface of brain 28). In some examples, IMD 16 may provide cortical stimulation therapy to patient 12, e.g., by delivering electrical stimulation to one or more tissue sites in the cortex of brain 28. In some examples, IMD 16 may provide vagal nerve stimulation (VNS) therapy to patient 12 by delivering electrical stimulation to one or more vagal nerve tissue sites.

In still other examples, IMD 16 may provide spinal cord stimulation (SCS), pelvic stimulation, gastric stimulation, peripheral nerve stimulation, functional electrical stimulation or delivery of pharmaceutical agent, insulin, pain relieving agent or anti-inflammatory agent to a target tissue site within a patient. Thus, although electrical stimulation therapy is primarily referred to throughout the remainder of the application, in other examples, therapy system 10 may be configured to deliver other types of therapy in addition to or instead of electrical stimulation therapy.

In the example shown in FIG. 1, IMD 16 may be implanted within a subcutaneous pocket in the pectoral region of patient 12. In other examples, IMD 16 may be implanted within other regions of patient 12, such as a subcutaneous pocket in the abdomen or buttocks of patient 12 or proximate the cranium of patient 12. Implanted lead extension 18 is coupled to IMD 16 via connector block 30 (also referred to as a header), which may include, for example, electrical contacts that electrically couple to respective electrical contacts on lead extension 18. The electrical contacts electrically couple the electrodes 24, 26 carried by leads 20 to IMD 16. Lead extension 18 traverses from the implant site of IMD 16 within a chest cavity of patient 12, along the neck of patient 12 and through the cranium of patient 12 to access brain 28. IMD 16 can be constructed of a biocompatible material that resists corrosion and degradation from bodily fluids. IMD 16 may comprise a hermetic housing 34 to substantially enclose components, such as a processor, therapy module, and memory.

In the example shown in FIG. 1, leads 20 are implanted within the right and left hemispheres, respectively, of brain 28 in order to deliver electrical stimulation to one or more regions of brain 28, which may be selected based on many factors, such as the type of patient condition for which therapy system 10 is implemented to manage. Other implant sites for leads 20 and IMD 16 are contemplated. For example, IMD 16 may be implanted on or within cranium 32 or leads 20 may be implanted within the same hemisphere at multiple target tissue sites or IMD 16 may be coupled to a single lead that is implanted in one or both hemispheres of brain 28.

Leads 20 may be positioned to deliver electrical stimulation to one or more target tissue sites within brain 28 to manage patient symptoms associated with a disorder of patient 12. Leads 20 may be implanted to position electrodes 24, 26 at desired locations of brain 28 through respective holes in cranium 32. Leads 20 may be placed at any location within brain 28 such that electrodes 24, 26 are capable of providing electrical stimulation to target tissue sites within brain 28 during treatment. Different neurological or psychiatric disorders may be associated with activity in one or more of regions of brain 28, which may differ between patients. For example, a suitable target therapy delivery site within brain 28 for controlling a movement disorder of patient 12 may include one or more of the pedunculopontine nucleus (PPN), thalamus, basal ganglia structures (e.g., globus pallidus, substantia nigra or subthalamic nucleus), zona inserta, fiber tracts, lenticular fasciculus (and branches thereof), ansa lenticularis, and/or the Field of Forel (thalamic fasciculus). The PPN may also be referred to as the pedunculopontine tegmental nucleus.

As another example, in the case of MDD, bipolar disorder, OCD, or other anxiety disorders, leads 20 may be implanted to deliver electrical stimulation to the anterior limb of the internal capsule of brain 28, and only the ventral portion of the anterior limb of the internal capsule (also referred to as a VC/VS), the subgenual component of the cingulate cortex (which may be referred to as CG25), anterior cingulate cortex Brodmann areas 32 and 24, various parts of the prefrontal cortex, including the dorsal lateral and medial pre-frontal cortex (PFC) (e.g., Brodmann area 9), ventromedial prefrontal cortex (e.g., Brodmann area 10), the lateral and medial orbitofrontal cortex (e.g., Brodmann area 11), the medial or nucleus accumbens, thalamus, intralaminar thalamic nuclei, amygdala, hippocampus, the lateral hypothalamus, the Locus ceruleus, the dorsal raphe nucleus, ventral tegmentum, the substantia nigra, subthalamic nucleus, the inferior thalamic peduncle, the dorsal medial nucleus of the thalamus, the habenula, the bed nucleus of the stria terminalis, or any combination thereof. Target tissue sites not located in brain 28 of patient 12 are also contemplated.

As another example, in the case of a seizure disorder or Alzheimer's disease, for example, leads 20 may be implanted to deliver electrical stimulation to regions within the Circuit of Papez, such as, e.g., the anterior thalamic nucleus, the internal capsule, the cingulate, the fornix, the mammillary bodies, the mammillothalamic tract (mammillothalamic fasciculus), and/or hippocampus. For example, in the case of a seizure disorder, IMD 16 may deliver therapy to a region of brain 28 via a selected subset of electrodes 24, 26 to suppress cortical activity within the anterior thalamic nucleus, hippocampus, or other brain region associated with the occurrence of seizures (e.g., a seizure focus of brain 28). Conversely, in the case of Alzheimer's disease, IMD 16 may deliver therapy to a region of brain 28 via electrodes 24, 26 to increase cortical activity within the anterior thalamic nucleus, hippocampus, or other brain region associated with Alzheimer's disease. As another example, in the case of depression (e.g., MDD), IMD 16 may deliver therapy to a region of brain 28 via electrodes 24, 26 to increase cortical activity within one or more regions of brain 28 to effectively treat the patient disorder. As another example, IMD 16 may deliver therapy to a region of brain 28 via electrodes 24, 26 to decrease cortical activity within one or more regions of brain 28, such as, e.g., the frontal cortex, to treat the disorder.

Although leads 20 are shown in FIG. 1 as being coupled to a common lead extension 18, in other examples, leads 20 may be coupled to IMD 16 via separate lead extensions or directly coupled to IMD 16. Moreover, although FIG. 1 illustrates system 10 as including two leads 20A and 20B coupled to IMD 16 via lead extension 18, in some examples, system 10 may include one lead or more than two leads.

Leads 20 may be implanted within a desired location of brain 28 via any suitable technique, such as through respective burr holes in the skull of patient 12 or through a common burr hole in the cranium 32. Leads 20 may be placed at any location within brain 28 such that electrodes 24, 26 of leads 20 are capable of providing electrical stimulation to targeted tissue during treatment. Electrical stimulation generated from the stimulation generator (not shown) within the therapy module of IMD 16 may help mitigate the symptoms of movement disorders, such as by improving the performance of motor tasks by patient 12 that may otherwise be difficult. These tasks may include, for example, at least one of initiating movement, maintaining movement, grasping and moving objects, improving gait and balance associated with narrow turns, and the like. The exact therapy parameter values of the electrical stimulation therapy that may help mitigate symptoms of the movement disorder (or other patient condition) may be specific for the particular target stimulation site (e.g., the region of the brain) involved as well as the particular patient and patient condition.

In the examples shown in FIG. 1, electrodes 24, 26 of leads 20 are shown as ring electrodes. Ring electrodes may be relatively easy to program and are typically capable of delivering an electrical field to any tissue adjacent to leads 20. In other examples, electrodes 24, 26 of leads 20 may have different configurations. For example, electrodes 24, 26 of leads 20 may have a complex electrode array geometry that is capable of producing shaped electrical fields, including interleaved stimulation. An example of a complex electrode array geometry, may include an array of electrodes positioned at different axial positions along the length of a lead, as well as at different angular positions about the periphery, e.g., circumference, of the lead. The complex electrode array geometry may include multiple electrodes (e.g., partial ring or segmented electrodes) around the perimeter of each lead 20, in addition to, or instead of, a ring electrode. In this manner, electrical stimulation may be directed to a specific direction from leads 20 to enhance therapy efficacy and reduce possible adverse side effects from stimulating a large volume of tissue. In some examples in which multiple leads 20 are implanted on the same hemisphere surrounding a target, steered electrical stimulation can be performed in between two or more electrodes.

In some examples, outer housing 34 of IMD 16 may include one or more stimulation and/or sensing electrodes. For example, housing 34 can comprise an electrically conductive material that is exposed to tissue of patient 12 when IMD 16 is implanted in patient 12, or an electrode can be attached to housing 34. In other examples, leads 20 may have shapes other than elongated cylinders as shown in FIG. 1 with active or passive tip configurations. For example, leads 20 may be paddle leads, spherical leads, bendable leads, or any other type of shape effective in treating patient 12.

IMD 16 may deliver electrical stimulation therapy to brain 28 of patient 12 according to one or more stimulation therapy programs. A stimulation therapy program may define one or more electrical stimulation parameter values for therapy generated by a therapy module of IMD 16 and delivered from IMD 16 to brain 28 of patient 12. Where IMD 16 delivers electrical stimulation in the form of electrical pulses, for example, the electrical stimulation parameters may include amplitude mode (constant current or constant voltage), pulse amplitude, pulse width, a waveform shape, etc. In addition, if different electrodes are available for delivery of stimulation, a therapy parameter of a therapy program may be further characterized by an electrode combination, which may define selected electrodes and their respective polarities.

In some examples, IMD 16 is configured to deliver electrical stimulation therapy to brain 28 of patient 12 in an open loop manner, in which IMD 16 delivers the stimulation therapy without intervention from a user or a sensor. In other examples, IMD 16 is configured to deliver electrical stimulation therapy to brain 28 of patient 12 in a closed loop manner, in which IMD 16 controls the timing of the delivery of electrical stimulation to brain 28, the output parameters of the electrical stimulation, or both based on one or more of user input and input from a sensor. The sensor may, for example, provide feedback that may be used to control the electrical stimulation output from IMD 16.

In addition to being configured to deliver therapy to manage a disorder of patient 12, therapy system 10 is configured to sense bioelectrical signals of patient 12 (e.g., bioelectrical brain signals in the example of FIG. 1). It should be understood that the sensing of bioelectrical signals is not necessary in all examples. For example, for motion disorders, the signals may be generated from an accelerometer or some other device, and not necessarily from a bioelectrical signal. However, the techniques described in this disclosure are extendable to examples based on the sensing of bioelectrical signals. In general, the techniques described in this disclosure are applicable to examples where the patient generates a patient signal indicative of a patient condition. The patient signal may be a signal outputted by an accelerometer in response to a patient tremor. As another example, the patient signal may be a bioelectrical signal. Other possibilities of patient signals exist and the techniques described in this disclosure should not be construed as limited to the example patient signals described in this disclosure.

In some examples, IMD 16 may include a sensing module that is configured to sense bioelectrical signals within one or more regions of brain 28 via a subset of electrodes 24, 26, another set of electrodes, or both. Accordingly, in some examples, electrodes 24, 26 may be used to deliver electrical stimulation from the therapy module to target sites within brain 28 as well as sense brain signals within brain 28. However, IMD 16 can also use a separate set of sensing electrodes to sense the bioelectrical brain signals. In the example shown in FIG. 1, the signals generated by electrodes 24, 26 are conducted to the sensing module within IMD 16 via conductors within the respective lead 20A, 20B. In some examples, the sensing module of IMD 16 may sense bioelectrical signals via one or more of the electrodes 24, 26 that are also used to deliver electrical stimulation to brain 28. In other examples, one or more of electrodes 24, 26 may be used to sense bioelectrical signals while one or more different electrodes 24, 26 may be used to deliver electrical stimulation.

Depending on the particular stimulation electrodes and sense electrodes used by IMD 16, IMD 16 may monitor bioelectrical signals and deliver electrical stimulation at the same region of brain 28 or at different regions of brain 28. In some examples, the electrodes used to sense bioelectrical signals may be located on the same lead used to deliver electrical stimulation, while in other examples, the electrodes used to sense bioelectrical signals may be located on a different lead than the electrodes used to deliver electrical stimulation. In some examples, a bioelectrical signal of patient 12 may be monitored with external electrodes, e.g., scalp electrodes. Moreover, in some examples, the sensing module that senses bioelectrical signals of brain 28 (e.g., the sensing module that generates an electrical signal indicative of the activity within brain 28) is in a physically separate housing from outer housing 34 of IMD 16. However, in the example shown in FIG. 1 and the example primarily referred to herein for ease of description, the sensing module and therapy module of IMD 16 are enclosed within a common outer housing 34.

The bioelectrical signals sensed by IMD 16 may reflect changes in electrical current produced by the sum of electrical potential differences across brain tissue. Example bioelectrical brain signals include, but are not limited to, an electroencephalogram (EEG) signal, an electrocorticogram (ECoG) signal, a local field potential (LFP) sensed from within one or more regions of a patient's brain, and/or action potentials from single cells within the patient's brain. In some examples, LFP data can be measured ipsilaterally or contralaterally and considered as an average (e.g., a maximum or minimum or a heuristic combination thereof) or as some other value. The location at which the sensed signals are obtained may be adjusted to a disease onset side of the body of patient 12 or severity of symptoms or disease duration. The adjustments, may, for example, be made on the basis of clinical symptoms presented and their severity, which can be augmented or annotated with recorded LFP data. A clinician or a processor of IMD 16 may also add heuristic weights to ipsilaterally and/or contralaterally measured LFP data to be considered for system feedback.

External programmer 14 is configured to wirelessly communicate with IMD 16 as needed to provide or retrieve therapy information. Programmer 14 is an external computing device that the user, e.g., the clinician and/or patient 12, may use to communicate with IMD 16. For example, programmer 14 may be a clinician programmer that the clinician uses to communicate with IMD 16 and program one or more therapy programs for IMD 16. In addition, or instead, programmer 14 may be a patient programmer that allows patient 12 to select programs and/or view and modify therapy parameter values. The clinician programmer may include more programming features than the patient programmer. In other words, more complex or sensitive tasks may only be allowed by the clinician programmer to prevent an untrained patient from making undesired changes to IMD 16.

Programmer 14 may be a hand-held computing device with a display viewable by the user and an interface for providing input to programmer 14 (i.e., a user input mechanism). For example, programmer 14 may include a small display screen (e.g., a liquid crystal display (LCD) or a light emitting diode (LED) display) that presents information to the user. In addition, programmer 14 may include a touch screen display, keypad, buttons, a peripheral pointing device or another input mechanism that allows the user to navigate though the user interface of programmer 14 and provide input. If programmer 14 includes buttons and a keypad, the buttons may be dedicated to performing a certain function, i.e., a power button, the buttons and the keypad may be soft keys that change in function depending upon the section of the user interface currently viewed by the user, or any combination thereof. Alternatively, the screen (not shown) of programmer 14 may be a touch screen that allows the user to provide input directly to the user interface shown on the display. The user may use a stylus or their finger to provide input to the display.

In other examples, programmer 14 may be a larger workstation or a separate application within another multi-function device, rather than a dedicated computing device. For example, the multi-function device may be a notebook computer, tablet computer, workstation, cellular phone, personal digital assistant or another computing device that may run an application that enables the computing device to operate as a secure medical device programmer 14. A wireless adapter coupled to the computing device may enable secure communication between the computing device and IMD 16.

When programmer 14 is configured for use by the clinician, programmer 14 may be used to transmit initial programming information to IMD 16. This initial information may include hardware information, such as the type of leads 20, the arrangement of electrodes 24, 26 on leads 20, the position of leads 20 within brain 28, initial programs defining therapy parameter values, and any other information that may be useful for programming into IMD 16. Programmer 14 may also be capable of completing functional tests (e.g., measuring the impedance of electrodes 24, 26 of leads 20).

The clinician may also generate and store therapy programs within IMD 16 with the aid of programmer 14. During a programming session, the clinician may determine one or more therapy programs that may provide efficacious therapy to patient 12 to address symptoms associated with the movement disorder (or other patient conditions). For example, the clinician may select one or more electrode combinations with which stimulation is delivered to brain 28. During the programming session, patient 12 may provide feedback to the clinician as to the efficacy of the specific program being evaluated or the clinician may evaluate the efficacy based on one or more sensed or observable physiological parameters of patient (e.g., muscle activity) or based on motion detected via one or more motion sensors that generate signals indicative of motion of patient 12. Programmer 14 may assist the clinician in the creation/identification of therapy programs by providing a methodical system for identifying potentially beneficial therapy parameter values.

Programmer 14 may also be configured for use by patient 12. When configured as a patient programmer, programmer 14 may have limited functionality (compared to a clinician programmer) in order to prevent patient 12 from altering critical functions of IMD 16 or applications that may be detrimental to patient 12.

Whether programmer 14 is configured for clinician or patient use, programmer 14 is configured to communicate to IMD 16 and, optionally, another computing device, via wireless communication. Programmer 14, for example, may communicate via wireless communication with IMD 16 using radio frequency (RF) telemetry techniques known in the art. Programmer 14 may also communicate with another programmer or computing device via a wired or wireless connection using any of a variety of local wireless communication techniques, such as RF communication according to the 802.11 or Bluetooth specification sets, infrared (IR) communication according to the IRDA specification set, or other standard or proprietary telemetry protocols. Programmer 14 may also communicate with other programming or computing devices via exchange of removable media, such as magnetic or optical disks, memory cards or memory sticks. Further, programmer 14 may communicate with IMD 16 and another programmer via remote telemetry techniques known in the art, communicating via a local area network (LAN), wide area network (WAN), public switched telephone network (PSTN), or cellular telephone network, for example.

In accordance with the example techniques described in this disclosure, IMD 16 may be configured to deliver therapy to patient 12 in a closed loop manner. For example, a circuit within IMD 16 (e.g., a phase locked loop (PLL) circuit) may receive a patient signal indicative of a patient condition, and based on the received patient signal, the circuit may generate a timing signal. IMD 16 may deliver therapy based on the timing signal. As an example, IMD 16 may deliver a burst of therapy, e.g., a burst of stimulation pulses, based on a phase of the timing signal. Therefore, how often and when IMD 16 delivers therapy may be based on the frequency and phase of the timing signal. Also, because the timing signal is based on the received patient signal (at least initially as described in more detail), IMD 16 may be considered as functioning in a closed loop.

As an example, IMD 16 may include an accelerometer that generates a patient signal representing patient tremor. IMD 16 need not necessarily include the accelerometer, and the accelerometer may be located elsewhere in patient 12. In such examples, IMD 16 receives the patient signal from the accelerometer.

The PLL circuit may generate the timing signal from the received patient signal indicative of a patient condition. The frequency and phase of the timing signal may be the same as the frequency and phase of the received patient signal (or the frequency may be a multiple or factor of the frequency of the patient signal). IMD 16 may then deliver therapy based on the timing signal. For example, IMD 16 may compare a phase of the timing signal to a threshold phase and deliver a burst of therapy when the phase of the timing signal is equal to the threshold phase. As an illustration, IMD 16 may determine when the phase of the timing signal is equal to 90° and/or 270°, as these phases may correspond to a peak and trough, respectively, of the timing signal. Because the timing signal may have the same frequency and phase as the patient signal (or a multiple or factor of the patient signal), when the phase of the timing signal is 90° or 270°, the patient signal may be at a peak or trough, respectively. By delivering a burst of therapy (e.g., a burst of stimulation pulses for a finite time between a peak and trough, or a trough and a peak) at peak or troughs of the patient signal, IMD 16 may be able to deliver therapy when the tremor symptoms are at their worst.

In some cases, rather than using a PLL circuit to generate the timing signal, it may be possible to directly use the patient signal to determine when to deliver therapy (i.e., the patient signal and the timing signal become the same signal). For example, IMD 16 may determine when the phase of the patient signal is equal to a threshold phase, and deliver a burst of therapy at the peak or trough of the patient signal.

Delivering therapy based on a timing signal generated from the patient signal (or where the patient signal is the same as the timing signal) allows for IMD 16 to provide "coupled" therapy. Coupled therapy refers to delivering therapy based on the patient signal, rather than a free running therapy that is uncoupled from the patient signal. In coupled therapy, the time when IMD 16 delivers therapy is based on the patient signal (i.e., therapy delivery is phase locked with the patient signal). In free running therapy (i.e., uncoupled therapy), the time when IMD 16 delivers therapy is not based on the patient signal, meaning that the frequency and phase of the signal used to determine when to deliver therapy is not based on the patient signal (i.e., uncoupled from the patient signal).

In some cases, providing coupled therapy provides better tremor suppression as compared to uncoupled therapy. In the techniques described in this disclosure, IMD 16 provides coupled therapy for proper timing of the therapy delivery based on the received patient signal. Then, when the symptoms are squelched, IMD 16 keeps providing therapy at the correct time utilizing the techniques described in this disclosure, resulting in achieving the benefits of coupled therapy even if the patient signal is no longer present (e.g., no longer being received by the PLL circuit), as described below in more detail.

While coupled therapy is preferable, for closed-loop systems, potential issues arise. In particular, the delivery of therapy provides symptom relief. But it was the existence of the symptom that causes a patient signal to exist in the first place. Therefore, therapy delivery squelches the patient signal. Because the timing signal was based on the patient signal, the timing signal may no longer be present (e.g., the PLL circuit no longer receives the patient signal or the amplitude of the patient signal is very low, such as lower than some threshold). Because the timing signal is no longer present (e.g., no longer being received), IMD 16 may deliver therapy at suboptimal times. For instance, once the tremor is lost, the therapy delivery becomes uncoupled since the patient signal is no longer being received.

The techniques described in disclosure describe ways in which to maintain the frequency of the timing signal even after the patient signal is no longer being received (i.e., the patient signal is no longer present or is not currently being sensed). For example, a circuit within IMD 16 (e.g., a PLL circuit) may receive a patient signal indicative of a patient condition (e.g., a signal from an accelerometer representing patient tremor). The PLL circuit may determine a timing signal based on the patient signal. Then, during a duration when the patient signal is not being received (e.g., due to the symptom relief or due to an inability to otherwise sense the signal), the PLL circuit may output the timing signal. The timing signal, outputted by the PLL circuit, may have a same frequency as a frequency of the timing signal that was determined from the patient signal. In other words, the PLL circuit maintains the frequency of the timing signal. IMD 16 may deliver therapy based on the outputted timing signal during at least a portion of the duration when the patient signal is not being received (e.g., because it is no longer present or because it has been squelched to below some threshold).

There may be various ways in which the PLL circuit may maintain the frequency of the timing signal. For example, the PLL circuit may include or be coupled to a storage circuit that stores information for outputting the timing signal (e.g., stores information needed to output the timing signal having the same frequency as the frequency of the timing signal that was determined from the patient signal). The PLL circuit may output the timing signal based on the stored information when the patient signal is not present.

In some examples, the PLL circuit includes a reference oscillator such as a voltage controlled oscillator (VCO). The reference oscillator may output the timing signal, and the frequency of the timing signal is based on the voltage level applied to the VCO. As one example, a storage circuit such as an integrator may store information representing a voltage level that causes the reference oscillator to output the timing signal having the same frequency as the frequency of the timing signal that was determined from the patient signal. As another example, the storage circuit includes a storage unit to store a digital value representing the voltage level, and a digital-to-analog (DAC) converter for converting the digital value to an analog voltage for applying the voltage to the VCO.

In some cases, the frequency of the timing signal may not be optimal for therapy delivery. For instance, due to physiological changes such as food consumed, sleep, stress, etc., the instances when IMD 16 delivers therapy may be suboptimal, and the symptoms may return. As an illustration, the consumption of alcoholic beverages may change the frequency of the tremors, meaning that therapy delivery is uncoupled. However, the PLL circuit, by design, may update the frequency of the timing signal to that of the received patient signal, and then IMD 16 may once again deliver coupled therapy even after the new patient signal is no longer being received (e.g., no longer present, no longer being sensed, below a threshold etc.).

In this manner, symptom relief may be achieved even when the patient signal is not available. In other words, even though there is loss of patient signal, the therapy delivery is still coupled therapy. Although there may be occasional changes, any perturbations (e.g., return of tremor) may nudge the PLL circuit to output the correct timing signal. In this manner, the delivery of therapy may be responsive to near-instantaneous, as well as long-term, changes in the frequency of the sensed patient signal.

It should be understood that although the above examples are described with respect to patient tremor being an example of a patient condition, the techniques described in this disclosure are not so limited. Patient tremor is described as an example simply to ease with understanding. The techniques described in this disclosure are applicable to other patient conditions as well.

Therapy system 10 may be implemented to provide chronic stimulation therapy to patient 12 over the course of several months or years. However, system 10 may also be employed on a trial basis to evaluate therapy before committing to full implantation. If implemented temporarily, some components of system 10 may not be implanted within patient 12. For example, patient 12 may be fitted with an external medical device, such as a trial stimulator, rather than IMD 16. The external medical device may be coupled to percutaneous leads or to implanted leads via a percutaneous extension. If the trial stimulator indicates DBS system 10 provides effective treatment to patient 12, the clinician may implant a chronic stimulator within patient 12 for relatively long-term treatment.

System 10 shown in FIG. 1 is merely one example of a therapy system that is configured to perform the techniques described in this disclosure. Systems with other configurations of leads, electrodes, and sensors are possible. For example, in other implementations, IMD 16 may be coupled to additional leads or lead segments having one or more electrodes positioned at different target tissue sites, which may be within brain 28 or outside of brain (e.g., proximate to a spinal cord of patient 12, a peripheral nerve of patient 12, a muscle of patient 12, or any other suitable therapy delivery site). The additional leads may be used for delivering different stimulation therapies to respective stimulation sites within patient 12 or for monitoring at least one physiological parameter of patient 12.

Additionally, in other examples, a system may include more than one 1 MB. For example, a system may include two IMDs coupled to respective one or more leads. Each IMD can deliver stimulation to a respective lateral side of patient 12 in some examples.

As another example configuration, a therapy system can include one or more leadless electrical stimulators (e.g., microstimulators having a smaller form factor than IMD 16 and may not be coupled to any separate leads). The leadless electrical stimulators can be configured to generate and deliver electrical stimulation therapy to patient 12 via one or more electrodes on an outer housing of the electrical stimulator. In examples including a plurality of leadless electrical stimulators, the leadless electrical stimulators can be implanted at different target tissue sites within patient 12. One electrical stimulator may act as a "master" module that coordinates the delivery of stimulation to patient 12 via the plurality of electrical stimulators.

In some examples, IMD 16 is not configured to deliver electrical stimulation therapy to brain of patient 12, but, rather, is only configured to sense one or more physiological parameters of patient 12, including a bioelectrical brain signal of patient 12. This type of IMD 16 may a patient monitoring device useful for diagnosing patient 12, monitoring a patient condition 12, or to train IMD 16 or another IMD for therapy delivery.

Figure 2:
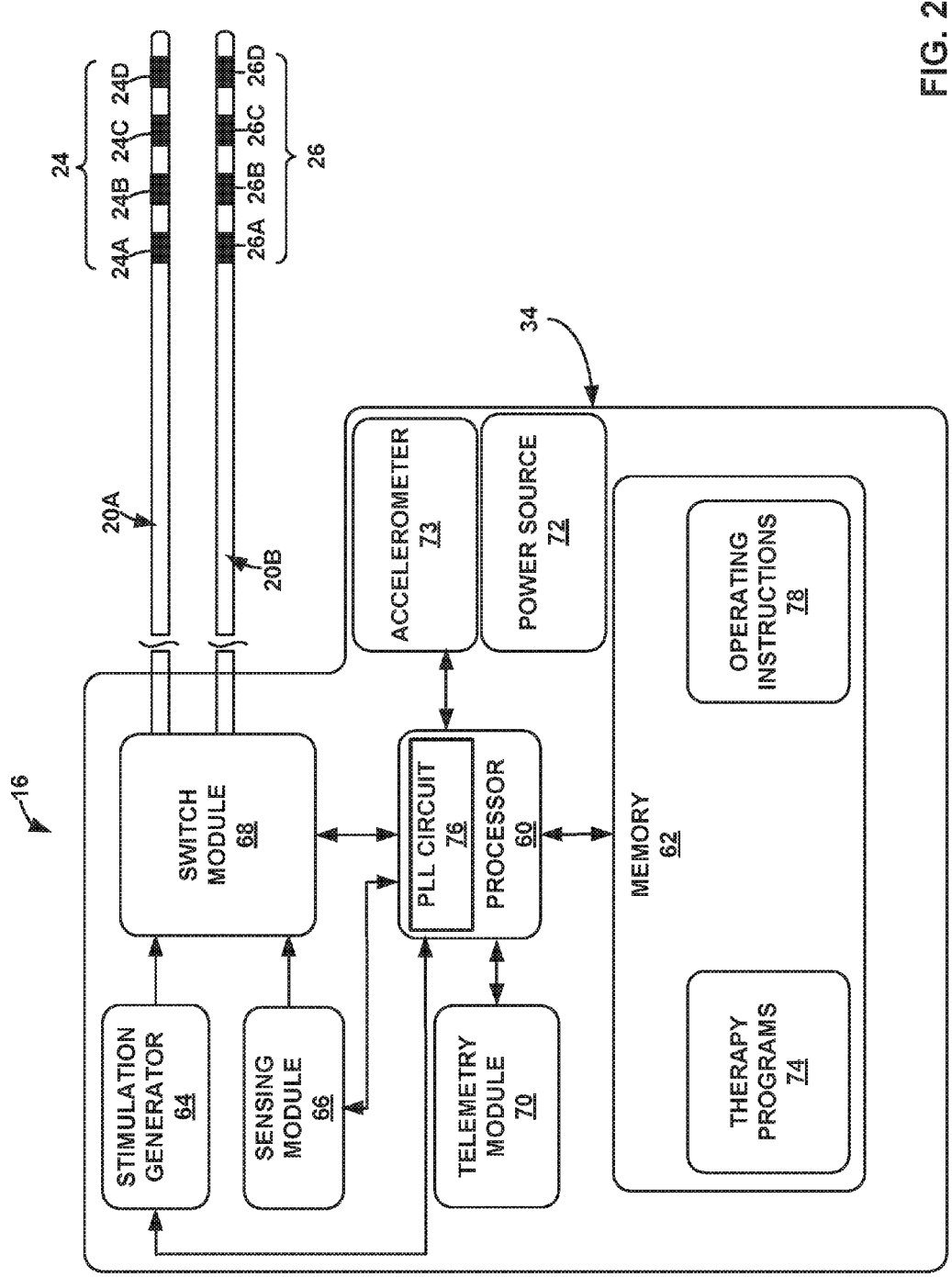
FIG. 2 is functional block diagram illustrating components of an example medical device.

FIG. 2 is functional block diagram illustrating components of an example IMD 16. In the example shown in FIG. 2, IMD 16 includes processor 60, memory 62, stimulation generator 64, sensing module 66, switch module 68, telemetry module 70, power source 72, and accelerometer 73. As illustrated, processor 60 includes phase lock loop (PLL) circuit 76. However, PLL circuit 76 need not necessarily be formed within processor 60, and may be external to processor 60, as well as formed within another component such as stimulation generator 64. For ease of description, PLL circuit 76 is described as being part of processor 60. Also, in some examples, PLL circuit 76 may be digital circuit or formed as software executing on hardware.

Memory 62, as well as other memories described herein, may include any volatile or non-volatile media, such as a random access memory (RAM), read only memory (ROM), non-volatile RAM (NVRAM), electrically erasable programmable ROM (EEPROM), flash memory, and the like. Memory 62 may store computer-readable instructions that, when executed by processor 60, cause IMD 16 to perform various functions described herein.

In the example shown in FIG. 2, memory 62 stores therapy programs 74 and operating instructions 78 (e.g., in separate memories within memory 62 or separate areas within memory 62). Each stored therapy program 74 defines a particular program of therapy in terms of respective values for electrical stimulation parameters, such as a stimulation electrode combination, electrode polarity, current or voltage amplitude, and, if stimulation generator 64 generates and delivers stimulation pulses, the therapy programs may define values for a pulse width, and pulse rate of a stimulation signal.

In some examples, memory 62 may also store brain signal data generated by sensing module 66 via at least one of electrodes 24, 26 and, in some cases, at least a portion of outer housing 34 of IMD 16, an electrode on outer housing 34 of IMD 16 or another reference. In addition, in some examples, processor 60 may append a time and date stamp to the brain signal data in memory 62. Operating instructions 78 guide general operation of IMD 16 under control of processor 60, and may include instructions for monitoring brains signals within one or more brain regions via electrodes 24, 26 and delivering electrical stimulation therapy to patient 12. Stimulation generator 64, under the control of processor 60, generates stimulation signals for delivery to patient 12 via selected combinations of electrodes 24, 26. In some examples, stimulation generator 64 generates and delivers stimulation signals to one or more target regions of brain 28 (FIG. 1), via a select combination of electrodes 24, 26, based on one or more stored therapy programs 74. The target tissue sites within brain 28 for stimulation signals or other types of therapy and stimulation parameter values may depend on the patient condition for which therapy system 10 is implemented to manage. While stimulation pulses are described, stimulation signals may be of any form, such as continuous-time signals (e.g., sine waves) or the like.

The processors described in this disclosure, including processor 60, may include one or more digital signal processors (DSPs), general purpose microprocessors, application specific integrated circuits (ASICs), field programmable logic arrays (FPGAs), or other equivalent integrated or discrete logic circuitry, or combinations thereof. The functions attributed to processors described herein may be provided by a hardware device and embodied as software, firmware, hardware, or any combination thereof. Processor 60 is configured to control stimulation generator 64 according to therapy programs 74 stored by memory 62 to apply particular stimulation parameter values specified by one or more programs.

In the example shown in FIG. 2, the set of electrodes 24 of lead 20A includes electrodes 24A, 24B, 24C, and 24D, and the set of electrodes 26 of lead 20B includes electrodes 26A, 26B, 26C, and 26D. Processor 60 may control switch module 68 to apply the stimulation signals generated by stimulation generator 64 to selected combinations of electrodes 24, 26. In particular, switch module 68 may couple stimulation signals to selected conductors within leads 20, which, in turn, deliver the stimulation signals across selected electrodes 24, 26. Switch module 68 may be a switch array, switch matrix, multiplexer, or any other type of switching module configured to selectively couple stimulation energy to selected electrodes 24, 26 and to selectively sense bioelectrical brain signals with selected electrodes 24, 26. Hence, stimulation generator 64 is coupled to electrodes 24, 26 via switch module 68 and conductors within leads 20. In some examples, however, IMD 16 does not include switch module 68.

Switch module 68 is illustrated as merely one example. In some examples, IMD 16 may not include switch module 68. Rather, IMD 16 may include a plurality of stimulation sources such as current sources that sink or source current and/or a voltage sources that output a positive or a negative voltage. In such examples, each one of electrodes 24, 26 may be coupled to separate ones of the stimulation sources. In some examples, some of electrodes 24, 26 may be coupled to the same stimulation source, and others to another stimulation source, with the possibility that one stimulation source couples to a plurality of electrodes 24, 26. In examples where IMD 16 does not include switch module 68, processor 60 and/or stimulation generator 64 may selectively enable stimulation sources to deliver the stimulation. In some examples, in addition to including a plurality of stimulation sources for one or more electrodes 24, 26, IMD 16 may include switch module 68.

Stimulation generator 64 may be a single channel or multi-channel stimulation generator. In particular, stimulation generator 64 may be capable of delivering, a single stimulation pulse, multiple stimulation pulses or continuous signal including a plurality of frequency components at a given time via a single electrode combination or multiple stimulation pulses at a given time via multiple electrode combinations. In some examples, however, stimulation generator 64 and switch module 68 may be configured to deliver multiple channels on a time-interleaved basis. For example, switch module 68 may serve to time divide the output of stimulation generator 64 across different electrode combinations at different times to deliver multiple programs or channels of stimulation energy to patient 12.

Sensing module 66, under the control of processor 60, is configured to sense bioelectrical signals of patient 12 via a selected subset of electrodes 24, 26 or with one or more electrodes 24, 26 and at least a portion of a conductive outer housing 34 of IMD 16, an electrode on an outer housing of IMD 16 or another reference. Processor 60 may control switch module 68 to electrically connect sensing module 66 to selected electrodes 24, 26. In this way, sensing module 66 may selectively sense bioelectrical brain signals with different combinations of electrodes 24, 26 (and/or a reference other than an electrode 24, 26). Processor 60 may monitor the efficacy of therapy delivery by IMD 16 via the sensed bioelectrical brain signals and determine whether the efficacy of therapy delivery has changed, and, in response, generate a notification (e.g., to patient 12 or patient caretaker).

Although sensing module 66 is incorporated into a common housing 34 with stimulation generator 64 and processor 60 in FIG. 2, in other examples, sensing module 66 is in a separate outer housing from outer housing 34 of IMD 16 and communicates with processor 60 via wired or wireless communication techniques. In the techniques described in this disclosure, the patient signal sensed via sensing module 66 is one example of a patient signal indicative of a patient condition. For instance, the patient signal may be a sensed LFP signal.

Accelerometer 73 may generate a patient signal based on patient movement. As one example, accelerometer 73 may generate a patient signal having the same frequency as patient tremor. Accelerometer 73 may be utilized for purposes other than patient tremor detection. In addition, rather than or in addition to accelerometer 73, IMD 16 may include another device type such as a gyroscope that generates a patient signal based on patient movement, although for ease of reference, the remainder of the disclosure describes examples as using an accelerometer. In the techniques described in this disclosure, the patient signal outputted by accelerometer 73 is one example of a patient signal indicative of a patient condition.

Also, accelerometer 73 may not be necessary in every example. For instance, in examples where the techniques are for sensed patient signals such as those from sensing module 66, accelerometer 73 may not be necessary, but may still be included in housing 34. In examples where accelerometer 73 is used, accelerometer 73 need not necessarily reside within IMD 16, and may reside elsewhere, including surgically implanted locations within patient 12.

As illustrated, processor 60 receives the bioelectrical signal from sensing module 66 configured to sense the bioelectrical signal via one or more of electrodes 24, 26. Processor 60 also receives a signal from accelerometer 73. As described above, in the techniques described in this disclosure, the sensed bioelectrical signal and the signal received from accelerometer 73 are examples of a patient signal. There may be additional examples of patient signals, such as other signals that are generated by the patient or are generated in response to behavior. In general, the patient signal that processor 60 receives may be indicative of a patient condition (e.g., patient tremors).

PLL circuit 76 may be configured to receive the patient signal indicative of a patient condition and output a timing signal that processor 60 uses to determine when stimulation generator 64 delivers therapy. PLL circuit 76 includes a reference oscillator that outputs the timing signal. A voltage level applied to a reference oscillator may determine the frequency of the signal outputted by the reference oscillator (e.g., in examples where the reference oscillator is a voltage controlled oscillator (VCO)). PLL circuit 76 may increase or decrease the voltage level of that reference oscillator that generates the timing signal such that the phase of the timing signal is approximately the same as the phase of the patient signal, so that the timing signal and the patient signal are phase and frequency locked.

Processor 60 may compare a phase of the timing signal to a threshold phase, and when the phase of timing signal equals the threshold phase, processor 60 causes stimulation generator 64 to output a burst of stimulation therapy (e.g., short-term stimulation). In this example, therapy programs 74 may store the parameters for the stimulation therapy that stimulation generator 64 delivers in a burst.

As described above, if the patient signal is no longer present due to the delivery of therapy, PLL circuit 76 may lose lock. For example, the frequency of the signal outputted by PLL circuit 76 is based on the voltage level applied to the VCO, and the voltage level applied to the VCO is based on the received patient signal. For instance, the voltage level used to control the frequency outputted by the reference oscillator is based on the difference between the patient signal and the timing signal. When the patient signal is present, the voltage level applied to the reference oscillator is set based on the patient signal. If the patient signal is no longer present, the voltage level, used to control the frequency outputted by the reference oscillator, drifts from its set voltage level. The drift in the voltage level results in the frequency of the timing signal drifting from the frequency that was determined from the patient signal. The drift in the frequency of the timing signal results in stimulation generator 64 delivering therapy at suboptimal times, meaning that IMD 16 is delivering uncoupled therapy.

In the techniques described in this disclosure, PLL circuit 76 may include or be coupled to a storage circuit that stores information for outputting the timing signal. For example, the storage circuit stores information needed to output the timing signal having the same frequency as the frequency of the timing signal that was determined from the patient signal. In other words, the storage circuit stores information needed to maintain the frequency of the timing signal to be the same frequency as determined from the patient signal. There may be various types of storage circuits, and the techniques described in this disclosure are not limited to any specific way of implementing the storage circuit.

During a duration when the patient signal is not present, PLL circuit 76 may output the timing signal (e.g., output the timing signal having a same frequency as a frequency of the timing signal that was determined from the patient signal). Processor 60 may control delivery of electrical stimulation therapy based on the outputted timing signal. For example, stimulation generator 64 may then deliver therapy based on the outputted timing signal during at least a portion of the duration when the patient signal is not being received.

Telemetry module 70 is configured to support wireless communication between IMD 16 and an external programmer 14 or another computing device under the control of processor 60. Processor 60 of IMD 16 may receive, as updates to programs, values for various stimulation parameters such as amplitude and electrode combination, from programmer 14 via telemetry module 70. The updates to the therapy programs may be stored within therapy programs 74 portion of memory 62. Telemetry module 70 in IMD 16, as well as telemetry modules in other devices and systems described herein, such as programmer 14, may accomplish communication by RF communication techniques. In addition, telemetry module 70 may communicate with external medical device programmer 14 via proximal inductive interaction of IMD 16 with programmer 14. Accordingly, telemetry module 70 may send information to external programmer 14 on a continuous basis, at periodic intervals, or upon request from IMD 16 or programmer 14. For example, processor 60 may transmit brain state information to programmer 14 via telemetry module 70.

Power source 72 delivers operating power to various components of IMD 16. Power source 72 may include a small rechargeable or non-rechargeable battery and a power generation circuit to produce the operating power. Recharging may be accomplished through proximal inductive interaction between an external charger and an inductive charging coil within IMD 16. In some examples, power requirements may be small enough to allow IMD 16 to utilize patient motion and implement a kinetic energy-scavenging device to trickle charge a rechargeable battery. In other examples, traditional batteries may be used for a limited period of time.

Figure 3:
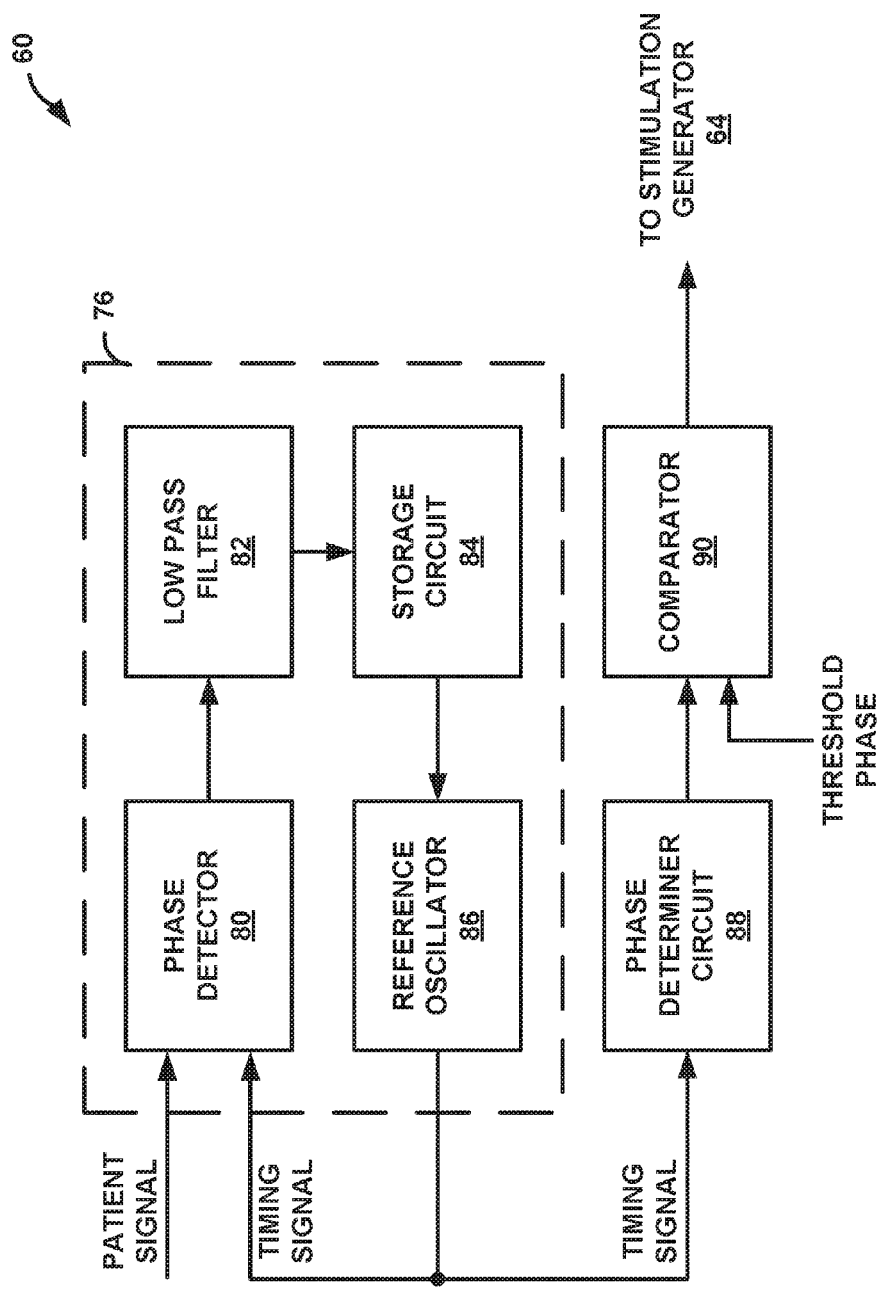
FIG. 3 is a block diagram illustrating an example of a phase locked loop (PLL) circuit.

FIG. 3 is a block diagram illustrating an example of a phase locked loop (PLL) circuit. For example, FIG. 3 illustrates PLL circuit 76 in more detail. To further illustrate the techniques described in this disclosure, FIG. 3 further illustrates components determining when therapy is delivered. Also, in FIG. 3, PLL circuit 76 is illustrated as being implemented as part of processor 60, but PLL circuit 76 need not necessarily be part of processor 60. PLL circuit 76 may be implement fully digital, fully analog, or a combination of digital and analog. PLL circuit 76 may be formed as an integrated circuit (IC) within processor 60 or external to processor 60, or some components may be internal to processor 60 and other external (e.g., reference oscillator 86). In some examples, PLL circuit 76 may be hardware executing software or firmware to implement some of the example functionality described below.

As illustrated, PLL circuit 76 includes phase detector 80, low pass filter 82, storage circuit 84, and reference oscillator 86. Phase detector 80 receives the patient signal and the timing signal outputted by reference oscillator 86, and outputs a voltage signal that is based on the differences between the phases of the patient signal and the timing signal. Low pass filter 82 low pass filters the voltage signal, and, in the example illustrated in FIG. 3, outputs the voltage signal to storage circuit 84.

Reference oscillator 86 receives the voltage signal from storage circuit 84, and the voltage level of the voltage signal sets the frequency at which reference oscillator 86 outputs the timing signal (e.g., in examples where reference oscillator 86 is a VCO). In this manner, the timing signal functions as negative feedback, and the loop that includes phase detector 80 and low pass filter 82 adjusts the voltage level of the voltage signal until reference oscillator 86 outputs the timing signal having a phase that is locked to a phase of the patient signal.

In addition to phase detector 80, phase determiner circuit 88 may receive the timing signal and determine the phase of the timing signal. There are many ways to determine the phase of the timing signal, and the techniques described in this disclosure should not be considered limited to a particular way in which to perform phase determination. Example ways for phase determination are described in U.S. Provisional Application No. 62/114,650, filed Feb. 11, 2015, and U.S. Provisional Application No. 62/083,038, filed Nov. 21, 2014, the entire content of each of which is incorporated herein by reference.

Phase determiner circuit 88 outputs the determined phase of the timing signal to comparator 90. Comparator 90 also receives a threshold phase (e.g., 90° or 270°), and determines when the determined phase of the timing signal equals the threshold phase. When the determined phase equals the threshold phase, comparator 90 outputs a signal to stimulation generator 64, causing stimulation generator 64 to deliver a burst of therapy (e.g., in the form of a burst of electrical stimulation pulses).

As described above, the delivery of therapy stimulation may cause the patient signal to no longer be present, and storage circuit 84 may store the information needed to output the timing frequency having the same frequency as the frequency of the timing signal determined from the patient signal. Accordingly, during a duration when the patient signal is not present, reference oscillator 86 outputs the timing signal based on the stored information. In this manner, the frequency of the timing signal does not drift even if the patient signal is no longer present.

There may be different examples of storage circuit 84. As one example, storage circuit 84 may be an integrator, and the integrator may output the same voltage signal when the patient signal is no longer present as it did when the patient signal was present. In this sense, although an integrator may not be considered as a storage circuit in a conventional sense, the integrator does keep the voltage signal that is outputted to reference oscillator 86 in a manner the same as when the patient signal was present, and functions as an equivalent storage circuit. Other examples of storage circuit 84 include a sample-and-hold circuit, or an analog-to-digital converter (ADC) that converts the voltage level to a digital value, a register to store the digital value, and a digital-to-analog converter (DAC) to convert the digital value back to an analog voltage level.

In the example illustrated in FIG. 3, storage circuit 84 is in series with the feedback loop of PLL circuit 76. However, the techniques described in this disclosure are not so limited. In some examples, storage circuit 84 may be selectively included to output the voltage signal to reference oscillator 86. For example, when the patient signal is present, storage circuit 84 may store the voltage level, and then, in response to the patient signal not being present, output the voltage level to reference oscillator 86. In such examples, storage circuit 84 may be a random access memory (RAM), local memory of processor 60, or other types of memory.

Over time it may be possible that the patient symptoms change, such as perturbations in the tremor due to changes in stress, diet, or other possible causes. In such situations, the patient signal may return but possibly with different characteristics (e.g., different frequency or phase). PLL circuit 76 may receive this new patient signal, and determine an updated timing signal that is locked to the patient signal. IMD 16 may then deliver therapy based on the updated timing signal, which, as above, squelches the patient signal. As above, storage circuit 84 stores information, and during a duration when the patient signal is not being received (due to previous therapy delivery), reference oscillator 86 outputs the updated timing signal having a same frequency as a frequency of the updated timing signal that was determined from the newly received patient signal. IMD 16 may control the delivery of therapy based on the updated timing signal during at least a portion of the duration when the second signal is not present.

It should be understood that the frequency of the timing signal and the frequency of the patient signal need not necessarily be the same frequency. For example, PLL circuit 76 may include a divider or multiplier in the feedback path, and the output of reference oscillator 86 may be a timing signal having a frequency that is a multiple or factor of the patient signal. Even in such examples, storage unit 84 may store information so that the frequency of the timing signal is the same as the timing signal that was determined from the patient signal, where in this example, the frequency of the timing signal is a multiple or factor of the patient signal.

Figure 4:
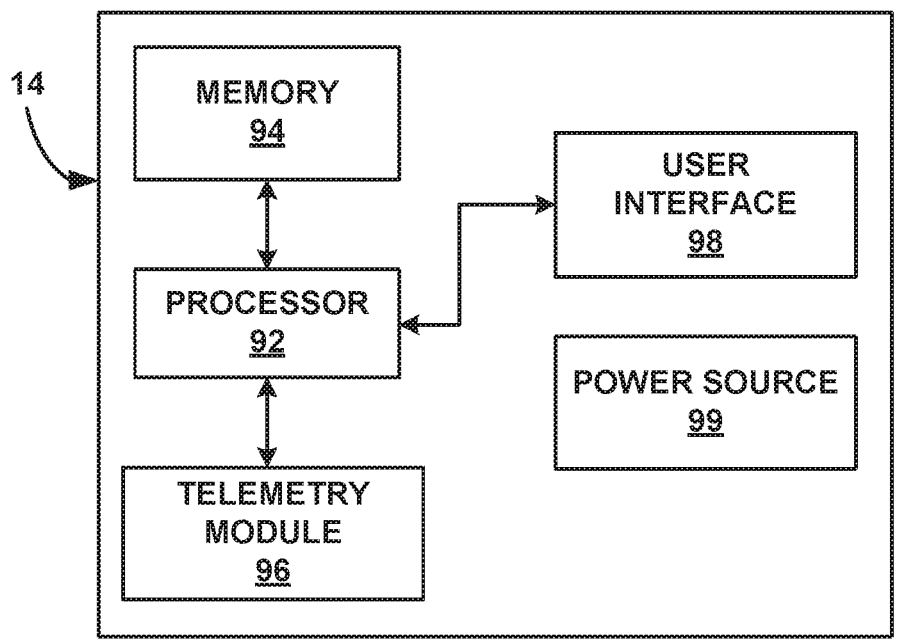
FIG. 4 is a functional block diagram illustrating components of an example medical device programmer.

FIG. 4 is a functional block diagram illustrating components of an example medical device programmer 14 (FIG. 1). Programmer 14 includes processor 92, memory 94, telemetry module 96, user interface 98, and power source 99. Processor 92 controls user interface 98 and telemetry module 96, and stores and retrieves information and instructions to and from memory 94. Programmer 14 may be configured for use as a clinician programmer or a patient programmer. Processor 92 may comprise any combination of one or more processors including one or more microprocessors, DSPs, ASICs, FPGAs, or other equivalent integrated or discrete logic circuitry. Accordingly, processor 92 may include any suitable structure, whether in hardware, software, firmware, or any combination thereof, to perform the functions ascribed herein to processor 92.

A user, such as a clinician or patient 12, may interact with programmer 14 through user interface 98. User interface 98 includes a display (not shown), such as a LCD or LED display or other type of screen, with which processor 92 may present information related to the therapy. In addition, user interface 98 may include an input mechanism to receive input from the user. The input mechanisms may include, for example, buttons, a keypad (e.g., an alphanumeric keypad), a peripheral pointing device or another input mechanism that allows the user to navigate though user interfaces presented by processor 92 of programmer 14 and provide input.

If programmer 14 includes buttons and a keypad, the buttons may be dedicated to performing a certain function (i.e., a power button), or the buttons and the keypad may be soft keys that change function depending upon the section of the user interface currently viewed by the user. In addition, or instead, the screen (not shown) of programmer 14 may be a touch screen that allows the user to provide input directly to the user interface shown on the display. The user may use a stylus or their finger to provide input to the display. In other examples, user interface 98 also includes audio circuitry for providing audible notifications, instructions or other sounds to patient 12, receiving voice commands from patient 12, which may be useful if patient 12 has limited motor functions, or both. Patient 12, a clinician or another user may also interact with programmer 14 to manually select therapy programs, generate new therapy programs, modify therapy programs through individual or global adjustments, and transmit the new programs to IMD 16. In some examples, at least some of the control of therapy delivery by IMD 16 may be implemented by processor 92 of programmer 14.

Memory 94 may include instructions for operating user interface 98 and telemetry module 96, and for managing power source 99. In some examples, memory 94 may also store any therapy data retrieved from IMD 16 during the course of therapy, biomarker information, sensed bioelectrical brain signals, and the like. In some instances, the clinician may use this therapy data to determine the progression of the patient condition in order to plan future treatment for the movement disorder (or other patient condition) of patient 12. Memory 94 may include any volatile or nonvolatile memory, such as RAM, ROM, EEPROM or flash memory. Memory 94 may also include a removable memory portion that may be used to provide memory updates or increases in memory capacities. A removable memory may also allow sensitive patient data to be removed before programmer 14 is used by a different patient.

Wireless telemetry in programmer 14 may be accomplished by RF communication or proximal inductive interaction of external programmer 14 with IMD 16. This wireless communication is possible through the use of telemetry module 96. Accordingly, telemetry module 96 may be similar to the telemetry module contained within IMD 16. In other examples, programmer 14 may be capable of infrared communication or direct communication through a wired connection. In this manner, other external devices may be capable of communicating with programmer 14 without needing to establish a secure wireless connection.

Power source 99 is configured to deliver operating power to the components of programmer 14. Power source 99 may include a battery and a power generation circuit to produce the operating power. In some examples, the battery may be rechargeable to allow extended operation. Recharging may be accomplished by electrically coupling power source 99 to a cradle or plug that is connected to an alternating current (AC) outlet. In addition, recharging may be accomplished through proximal inductive interaction between an external charger and an inductive charging coil within programmer 14. In other examples, traditional batteries (e.g., nickel cadmium or lithium ion batteries) may be used. In addition, programmer 14 may be directly coupled to an alternating current outlet to operate.

In some examples, PLL circuit 76 may determine a timing signal having a frequency based on the received patient signal, and processor 60 may output information of the timing signal to programmer 14. Processor 92 may store information in memory 94 for having PLL circuit 76 output the timing signal having the same frequency during a duration when the patient signal is not being received. Processor 92 may then control the delivery of therapy based on stored information. For example, processor 92 may output information instructing IMD 16 to deliver therapy every set number of milliseconds (ms).

Figure 5:
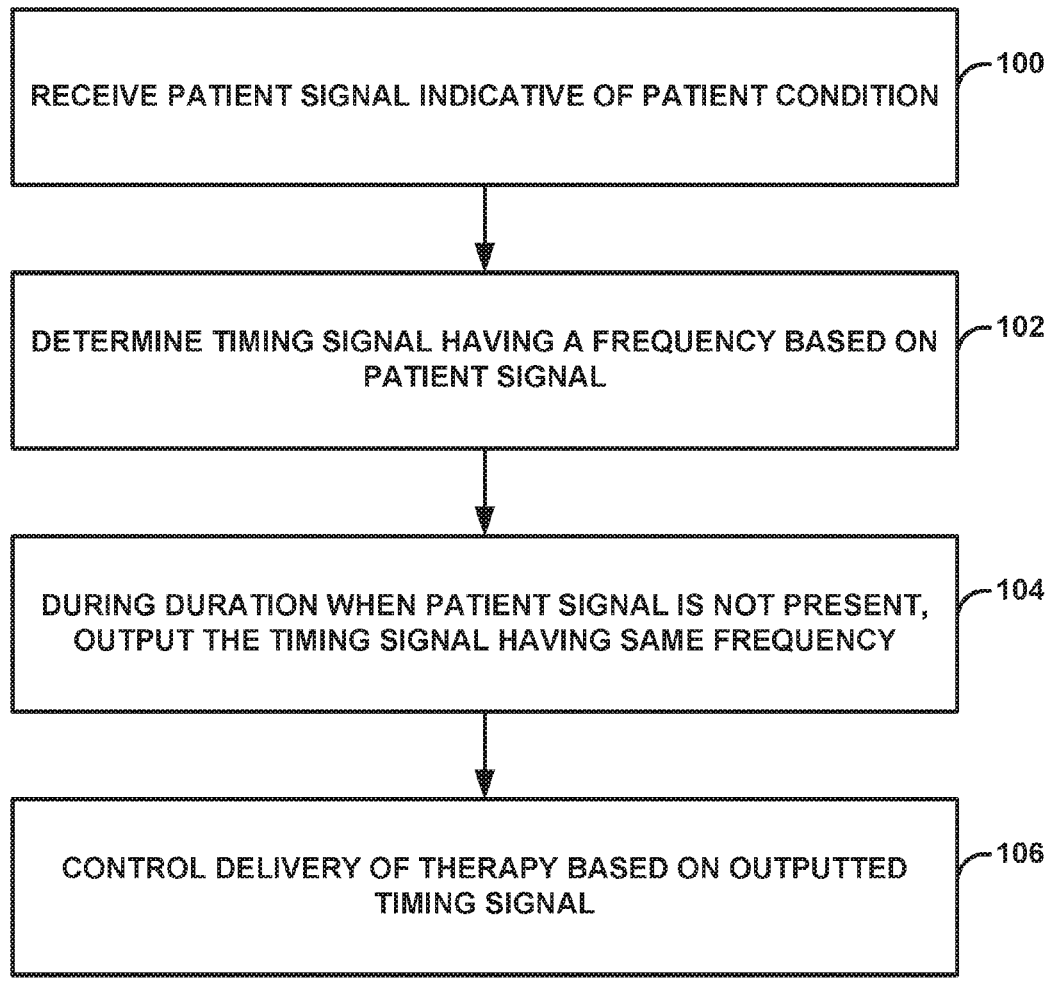
FIG. 5 is a flow diagram illustrating an example technique in accordance with one or more aspects of this disclosure.

FIG. 5 is a flow diagram illustrating an example technique in accordance with one or more aspects of this disclosure. In some examples, IMD 16 may perform the example techniques illustrated in FIG. 5.

PLL circuit 76 may receive a patient signal indicative of a patient condition (100), and may determine a timing signal having a frequency based on the patient signal (102). The patient signal may be sensed electrical signals, and may be an output of accelerometer 73 that represents patient tremor. Via the feedback, the voltage level outputted to reference oscillator 86 causes reference oscillator 86 to output a timing signal having a frequency that is the same or a multiple of the frequency of the patient signal.

During a duration when the patient signal is not present, reference oscillator 86 may output the timing signal (104). For example, reference oscillator 86 may output the timing signal having a same frequency as the frequency of the timing signal that was determined from the patient signal. Storage circuit 84 may store information for outputting the timing signal, and reference oscillator 86 may output the timing signal based on the stored information. For instance, storage circuit 84 may store information needed to output the timing signal having the same frequency as the frequency of the timing signal that was determined from the patient signal. In some examples, storage circuit 84 may store information representing a voltage level that is applied to reference oscillator 86 and that causes reference oscillator 86 to output the timing signal having the same frequency of the timing signal that was determined from the patient signal. One example of storage circuit 84 is an integrator, but other examples of storage circuit 84 exist such as sample-and-hold circuits, a combination of an ADC and digital register, and other examples.

IMD 16 and/or programmer 14 may control delivery of therapy based on the outputted timing signal (106). For example, stimulation generator 64 may deliver electrical stimulation therapy based on the outputted timing signal during at least a portion of the duration when the patient signal is not being received. For instance, in some examples, after determining the timing signal having a frequency based on the patient signal, processor 60 may control delivery, via stimulation generator 64, of a first instance of therapy based on the determined timing signal, where delivering the first instance of therapy causes the duration during which the patient signal is not being received (e.g., not present, below threshold, not sensed, etc.). In these examples, controlling the delivery of electrical stimulation therapy based on the outputted timing signal during at least a portion of when the patient signal is not being received is a second instance of therapy delivery after the delivery of the first instance of therapy.

In some examples, stimulation generator 64 may deliver therapy based on the outputted signal during the entire duration when the patient signal is not present (e.g., not being received), and then deliver therapy when the patient signal is present again (e.g., being received), due to changes in effectiveness of the therapy. Also, to determine when to deliver therapy, comparator 90 may compare the phase of the timing signal to that of the threshold phase, and cause stimulation generator 64 to deliver a burst of therapy when the phase of the timing signal equals the threshold phase.

Figure 6A:
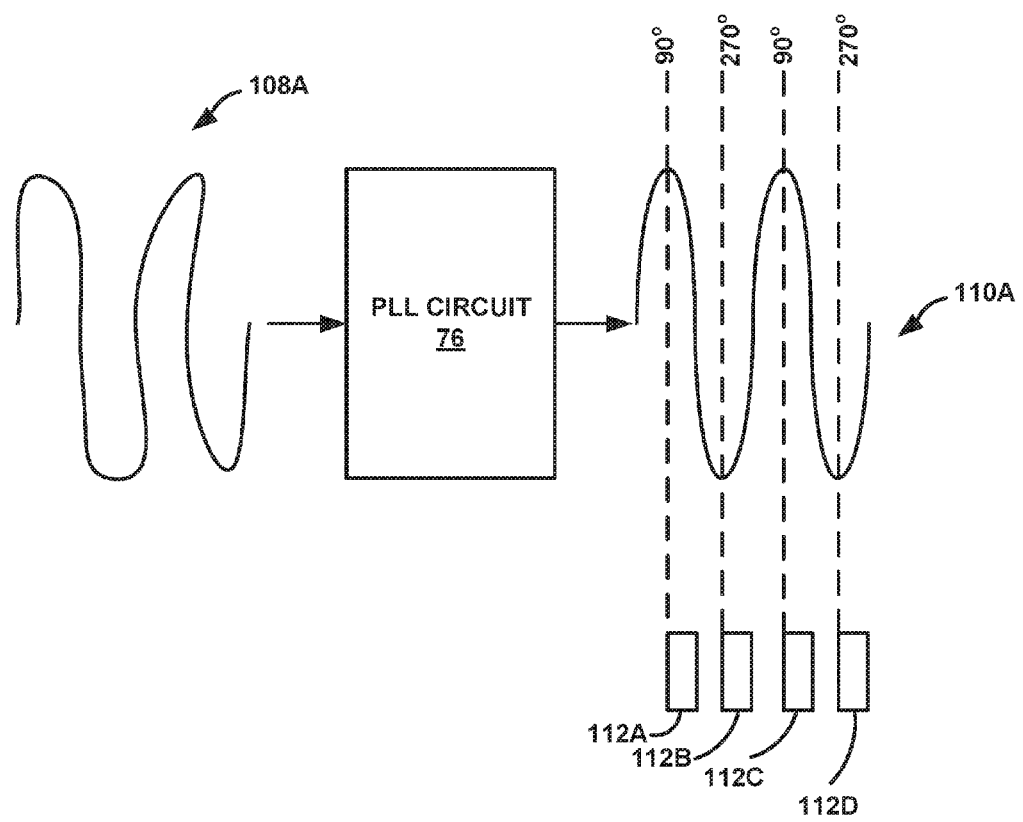
FIG. 6A is a conceptual diagram illustrating first instances of therapy delivery.
Figure 6B:
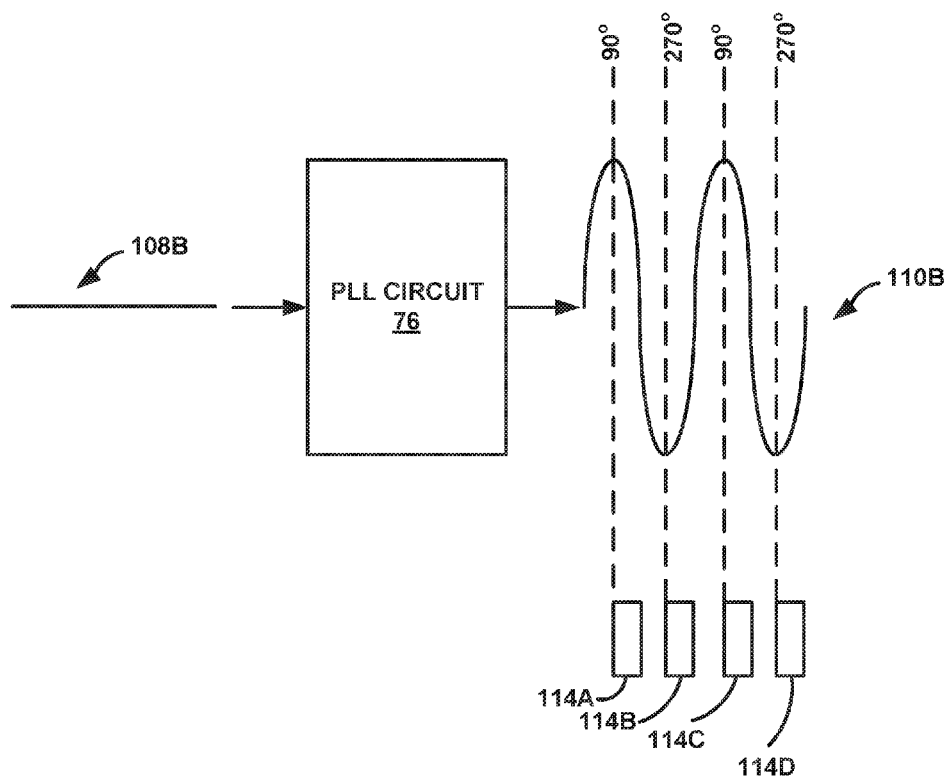
FIG. 6B is a conceptual diagram illustrating second instances of therapy delivery.

FIG. 6A is a conceptual diagram illustrating first instances of therapy delivery. FIG. 6B is a conceptual diagram illustrating second instances of therapy delivery. In the example illustrated in FIG. 6, PLL circuit 76 receives patient signal 108A (e.g., the output of accelerometer 73, a recorded LFP (local field potential) that tracks the patient tremor, or any other signal that track tremor), and outputs timing signal 110A. Timing signal 110A is phase and frequency locked with patient signal 108A (e.g., the frequency and phase of timing signal 110A is same as frequency and phase of patient signal 108A).

Phase determiner circuit 88 receives timing signal 110A and outputs the phase of timing signal 110A to comparator 90. Comparator 90 compares the received phase with a threshold phase and outputs a signal to stimulation generator 64 instructing stimulation generator 64 to output a burst of therapy.

For example, in FIG. 6A, the threshold phase is 90° and 270°, which happen to correspond to peaks and troughs of timing signal 110A, respectively. It should be understood that 90° and 270° as the threshold phase is provided for purposes of illustration only, and should not be considered limiting. In this example, in response to comparator 90 determining that the phase of timing signal 110A equals 90°, comparator 90 may cause stimulation generator 64 to deliver a burst of therapy 112A, and in response to comparator 90 determining that the phase of timing signal 110A equals 270°, comparator 90 may cause stimulation generator 64 to deliver a burst of therapy 112B. This process may then repeat, and in response to comparator 90 determining that the phase of timing signal 110A equals 90°, comparator 90 may cause stimulation generator 64 to deliver a burst of therapy 112C, and in response to comparator 90 determining that the phase of timing signal 110A equals 270°, comparator 90 may cause stimulation generator 64 to deliver a burst of therapy 112D, and so forth.

The duration of therapies 112A-112D is provided for purposes of illustration only and should not be considered limiting. Therapy programs 74 may store information indicative of the amplitude, duration, frequency, etc. of therapies 112A-112D. Therapies 112A-112D may be the same or two or more may be different from one another.

In some examples, the duration of therapies 112A-112D may be approximately ±45°. In some examples, stimulation generator 64 may not deliver therapies 112A-112D at exactly 90° or 270°, and there may be some delay when therapy is delivered or therapy may be delivered earlier than when the phase of timing signal 110A is 90° or 270°. In general, the timing and duration of therapies 112A-112D may be in range of ±45° relative to 90° phase of timing signal 110A, or ±45° relative to 270° phase of timing signal 110A, as appropriate.

The frequency of therapies 112A-112D may be between approximately 60 Hz and approximately 500 Hz, such as approximately 130 Hz. The voltage amplitude of therapies 112A-112D may be between approximately 0.1 volts and approximately 50 volts, such as between approximately 0.5 volts and approximately 20 volts, or approximately 5 volts. The current amplitude of therapies 112A-112D may be between approximately 0.2 mA to approximately 100 mA, such as between approximately 1 mA and approximately 40 mA, or approximately 10 mA. The pulse width may be based on the examples provided above (e.g., ±45°) or between approximately 10 microseconds and approximately 5000 microseconds, such as between approximately 10 microseconds and approximately 1000 microseconds, or between 30 microseconds and approximately 450 microseconds.

Accordingly, in some examples, stimulation generator 64 generates electrical stimulation signals (e.g., therapies 112A-112D) with the electrical stimulation parameters noted above. Other ranges of therapy parameters values may also be useful, and may depend on the target stimulation site within patient. While stimulation pulses are described, stimulation signals may be of any form, such as continuous-time signals (e.g., sine waves) or the like.

The delivery of therapies 112A-112D may result in symptom relief, and the result of symptom relief may be that patient signal 108A is no longer present. For example, as illustrated in FIG. 6B, after the delivery of one or more of a first instance of therapy delivery (e.g., delivery of one or more of therapies 112A-112D), the output of accelerometer 73 may be a constant signal 108B with no frequency content from which PLL circuit 76 can lock.

In the techniques described in this disclosure, although patent signal 108A is no longer present, PLL circuit 76 may be able to output a timing signal having a same frequency as a frequency of the timing signal that was determined from patient signal 108A. For example, during a duration when patient signal 108A is not present, PLL circuit 76 may output timing signal 110B having a same frequency as a frequency of timing signal 110A that was determined from patient signal 108A.

Stimulation generator 64 may deliver therapy based on outputted timing signal 110B during at least a portion of duration when patient signal 108A is not present. For example, phase determiner circuit 88 may determine the phase of timing signal 110B and output the phase to comparator 90. Similar to FIG. 6A, in response to comparator 90 determining that the phase of timing signal 110B equals 90°, comparator 90 may cause stimulation generator 64 to deliver a burst of therapy 114A, and in response to comparator 90 determining that the phase of timing signal 110B equals 270°, comparator 90 may cause stimulation generator 64 to deliver a burst of therapy 114B. This process may then repeat, and in response to comparator 90 determining that the phase of timing signal 110B equals 90°, comparator 90 may cause stimulation generator 64 to deliver a burst of therapy 114C, and in response to comparator 90 determining that the phase of timing signal 110B equals 270°, comparator 90 may cause stimulation generator 64 to deliver a burst of therapy 114D, and so forth.

The duration of therapies 114A-114D is provided for purposes of illustration only and should not be considered limiting. Therapy programs 74 may store information indicative of the amplitude, duration, frequency, etc. of therapies 114A-114D. Therapies 114A-114D may be the same or two or more may be different from one another, and may be the same or different from respective therapies 112A-112D.

For example, like therapies 112A-112D, the duration of therapies 114A-114D may be approximately ±45°. In some examples, stimulation generator 64 may not deliver therapies 114A-114D at exactly 90° or 270°, and there may be some delay when therapy is delivered or therapy may be delivered earlier than when the phase of timing signal 110B is 90° or 270°. In general, the timing and duration of therapies 114A-114D may be in range of ±45° relative to 90° phase of timing signal 110B, or ±45° relative to 270° phase of timing signal 110B, as appropriate.

The frequency of therapies 114A-114D may be between approximately 60 Hz and approximately 500 Hz, such as approximately 130 Hz. The voltage amplitude of therapies 114A-114D may be between approximately 0.1 volts and approximately 50 volts, such as between approximately 0.5 volts and approximately 20 volts, or approximately 5 volts. The current amplitude of therapies 114A-114D may be between approximately 0.2 mA to approximately 100 mA, such as between approximately 1 mA and approximately 40 mA, or approximately 10 mA. The pulse width may be based on the examples provided above (e.g., ±45°) or between approximately 10 microseconds and approximately 5000 microseconds, such as between approximately 10 microseconds and approximately 1000 microseconds, or between 30 microseconds and approximately 450 microseconds.

Accordingly, in some examples, stimulation generator 64 generates electrical stimulation signals (e.g., therapies 114A-114D) with the electrical stimulation parameters noted above. Other ranges of therapy parameters values may also be useful, and may depend on the target stimulation site within patient. While stimulation pulses are described, stimulation signals may be of any form, such as continuous-time signals (e.g., sine waves) or the like.

While the techniques described above are primarily described as being performed by processor 60 of IMD 16, in other examples, one or more other processors may perform any part of the techniques described herein alone or in addition to processor 60. Thus, reference to "a processor" may refer to "one or more processors." Likewise, "one or more processors" may refer to a single processor or multiple processors in different examples.

The techniques described in this disclosure, including those attributed to IMD 16, programmer 14, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as clinician or patient programmers, medical devices, or other devices.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the term "processor," as used herein may refer to one or more of any of the foregoing structure or any other structure suitable for implementation of the techniques described herein.

While some examples described above relate to delivery of DBS therapy to treat tremor, it will be understood that the techniques described in this disclosure may be utilized to deliver therapy to a patient to treat a variety of symptoms or patient conditions such as chronic pain, Parkinson's disease, other types of movement disorders, seizure disorders (e.g., epilepsy), urinary or fecal incontinence, sexual dysfunction, obesity, mood disorders (e.g., depression), gastroparesis or diabetes. Additionally, while the patient signal indicative of a patient condition may be based on patient movement as sensed by an accelerometer or gyroscope, the patient signal could alternatively or additionally be any physiological signal from which frequency information (frequency content and/or phase information) can be derived. This may include local field potential (LFP) signals or other physiological signals processed using filtering, Fourier transforms, or other processing techniques to extract that frequency information.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

Various examples have been described. These and other examples are within the scope of the following claims.

What is claimed is:

1. A method comprising:
   receiving, by a circuit, a patient signal indicative of a patient condition;
   determining, by the circuit, a first timing signal having a frequency based on the patient signal;
   controlling, by the circuit, delivery of a first instance of electrical stimulation therapy, with a stimulation generator, based on the first timing signal, wherein controlling delivery of the first instance of the electrical stimulation therapy comprises determining when to deliver the first instance of the electrical stimulation therapy based on the first timing signal, and wherein delivery of the first instance of the electrical stimulation therapy causes the patient signal to not be received for a duration;
   during the duration when the patient signal is not being received, generating, by the circuit, a second timing signal having the same frequency as the frequency of the first timing signal that was determined based on the patient signal; and
   controlling, by the circuit, delivery of a second instance of the electrical stimulation therapy, with the stimulation generator, based on the second timing signal during at least a portion of the duration when the patient signal is not being received, wherein controlling delivery of the second instance of the electrical stimulation therapy comprises determining when to deliver the second instance of the electrical stimulation therapy based on the second timing signal.

2. The method of claim 1, further comprising:
   storing information for the first timing signal,
   wherein generating the second timing signal comprises generating the second timing signal based on the stored information.

3. The method of claim 2, wherein storing information comprises storing, with an integrator, the information for the first timing signal.

4. The method of claim 2, wherein storing information comprises storing information representing a voltage level that causes a reference oscillator to output the second timing signal.

5. The method of claim 1, wherein receiving the patient signal comprises receiving, from an accelerometer, a signal representing patient tremor.

6. The method of claim 1, wherein the patient signal comprises a first patient signal, the method further comprising:
   receiving a second patient signal indicative of the patient condition;
   determining an updated timing signal based on the second patient signal;
   during a duration when the second patient signal is not being received, outputting the updated timing signal;
   controlling delivery of electrical stimulation therapy based on the updated timing signal during at least a portion of the duration when the second patient signal is not being received.

7. The method of claim 1, further comprising:
   comparing a phase of the second timing signal to a threshold phase,
   wherein controlling delivery of the second instance of the electrical stimulation therapy comprises controlling delivery of the second instance of the electrical stimulation therapy based on the comparison.

8. The method of claim 1, wherein controlling delivery of the second instance of the electrical stimulation therapy based on the second timing signal comprises delivering the second instance of the electrical stimulation therapy based on the second timing signal during the entire duration when the patient signal is not being received.

9. The method of claim 1, wherein the first instance of the electrical stimulation therapy comprises one or more pulses of the electrical stimulation therapy, and wherein the second instance of the electrical stimulation therapy comprises one or more pulses of the electrical stimulation therapy.

10. A medical device comprising:
    an electrical stimulation generator; and
    a circuit configured to:
       receive a patient signal indicative of a patient condition;
       determine a first timing signal having a frequency based on the patient signal; and determine when the electrical stimulation generator is to deliver a first instance of electrical stimulation therapy based on the first timing signal, wherein the electrical stimulation generator is configured to deliver the first instance of the electrical stimulation therapy based on the determination of when to deliver the first instance of the electrical stimulation therapy, and wherein delivery of the first instance of the electrical stimulation therapy causes the patient signal to not be received for a duration, wherein the circuit is configured to:
during the duration when the patient signal is not being received, generate a second timing signal having the same frequency as the frequency of the first timing signal that was determined based on the patient signal; and determine when the electrical stimulation generator is to deliver a second instance of the electrical stimulation therapy based on the second timing signal, wherein the electrical stimulation generator is configured to deliver the second instance of the electrical stimulation therapy, during at least a portion of the duration when the patient signal is not being received, based on the determination of when to deliver the second instance of the electrical stimulation therapy.

11. The medical device of claim 10, wherein the circuit comprises a phase locked loop (PLL) circuit.

12. The medical device of claim 10, further comprising:
a storage circuit configured to store information for the first timing signal,
wherein to generate the second timing signal, the circuit is configured to generate the second timing signal based on the stored information.

13. The medical device of claim 12, wherein the storage circuit comprises an integrator.

14. The medical device of claim 12, wherein the circuit comprises a reference oscillator, and wherein the storage circuit is configured to store information representing a voltage level that causes the reference oscillator to output the second timing signal.

15. The medical device of claim 10, wherein to receive the patient signal, the circuit is configured to receive, from an accelerometer, a signal representing patient tremor.

16. The medical device of claim 10, wherein the patient signal comprises a first patient signal, wherein the circuit is configured to:
receive a second patient signal indicative of the patient condition;
determine an updated timing signal based on the second patient signal; and
during a duration when the second patient signal is not being received, output the updated timing signal, and
wherein the electrical stimulation generator is configured to deliver electrical stimulation therapy based on the updated timing signal during at least a portion of the duration when the second patient signal is not being received.

17. The medical device of claim 10, further comprising:
a comparator circuit configured to compare a phase of the second timing signal to a threshold phase,
wherein the stimulation generator is configured to deliver the second instance of the electrical stimulation therapy based on the comparison.

18. The medical device of claim 10, wherein to deliver the second instance of the electrical stimulation therapy based on the second signal, the stimulation generator is configured to deliver the second instance of the electrical stimulation therapy based on the second timing signal during the entire duration when the patient signal is not being received.

19. A medical device comprising:
a stimulation generator; and
circuitry comprising:
means for receiving a patient signal indicative of a patient condition;
means for determining a first timing signal having a frequency based on the patient signal; and
means for determining when the electrical stimulation generator is to deliver a first instance of electrical stimulation therapy based on the first timing signal,
wherein the electrical stimulation generator is configured to deliver the first instance of the electrical stimulation therapy based on the determination of when to deliver the first instance of the electrical stimulation therapy, and wherein delivery of the first instance of the electrical stimulation therapy causes the patient signal to not be received for a duration,
wherein the circuitry further comprises:
means for generating a second timing signal having the same frequency as the frequency of the first timing signal that was determined based on the patient signal during the duration when the patient signal is not being received; and
means for determining when the electrical stimulation generator is to deliver a second instance of the electrical stimulation therapy based on the generated second timing signal,
wherein the stimulation generator is configured to deliver the second instance of the electrical stimulation therapy, during at least a portion of the duration when the patient signal is not being received, based on the determination of when to deliver the second instance of the electrical stimulation therapy.

20. The medical device of claim 19, wherein the circuitry further comprises:
means for storing information needed to generate the second timing signal having the same frequency as the frequency of the first timing signal that was determined from the patient signal,
wherein the means for generating the second timing signal comprises means for generating the second timing signal based on the stored information.

* * * * *